(12) United States Patent
Han et al.

(10) Patent No.: US 11,549,920 B2
(45) Date of Patent: Jan. 10, 2023

(54) METHOD FOR QUANTITATIVE ANALYSIS OF MONOMERS IN POLYIMIDE FILM

(71) Applicant: LG Chem, Ltd., Seoul (KR)

(72) Inventors: Su Youn Han, Daejeon (KR); Byoung Hyoun Kim, Daejeon (KR); Dong Hyun Kim, Daejeon (KR); Soo Ah Nam, Daejeon (KR); Bora Shin, Daejeon (KR)

(73) Assignee: LG Chem, Ltd.

( * ) Notice: Subject to any disclaimer, the term of this patent is extended or adjusted under 35 U.S.C. 154(b) by 678 days.

(21) Appl. No.: 16/484,021

(22) PCT Filed: Sep. 28, 2018

(86) PCT No.: PCT/KR2018/011481
§ 371 (c)(1),
(2) Date: Aug. 6, 2019

(87) PCT Pub. No.: WO2019/098524
PCT Pub. Date: May 23, 2019

(65) Prior Publication Data
US 2019/0391118 A1 Dec. 26, 2019

(30) Foreign Application Priority Data
Nov. 20, 2017 (KR) ........................ 10-2017-0154651

(51) Int. Cl.
*G01N 30/06* (2006.01)
*G01N 33/44* (2006.01)
*G01N 30/02* (2006.01)
*G01N 30/62* (2006.01)

(52) U.S. Cl.
CPC ........... *G01N 30/06* (2013.01); *G01N 33/442* (2013.01); *G01N 2030/027* (2013.01); *G01N 2030/067* (2013.01); *G01N 2030/626* (2013.01)

(58) Field of Classification Search
None
See application file for complete search history.

(56) References Cited

U.S. PATENT DOCUMENTS

| | | | |
|---|---|---|---|
| 5,543,493 | A | 8/1996 | Park et al. |
| 5,744,557 | A | 4/1998 | McCormick et al. |
| 2009/0192287 | A1 | 7/2009 | Ohtake et al. |
| 2011/0245455 | A1 | 10/2011 | Jeong et al. |
| 2016/0300810 | A1 | 10/2016 | Kanamori et al. |

FOREIGN PATENT DOCUMENTS

| | | |
|---|---|---|
| CN | 001128034 A | 7/1996 |
| CN | 101654489 A | 2/2010 |
| CN | 103713059 A | 4/2014 |
| CN | 106795644 A | 5/2017 |
| JP | H01292250 A | 11/1989 |
| JP | 2780393 B2 | 7/1998 |
| JP | 2002148254 A | 5/2002 |
| JP | 2004347334 A | 12/2004 |
| JP | 2006124530 A | 5/2006 |
| JP | 2010083922 A | 4/2010 |
| JP | 2011143678 A | 7/2011 |
| JP | 2017187475 A | 10/2017 |
| KR | 950029297 A | 11/1995 |
| KR | 20070083574 A | 8/2007 |
| KR | 20130035447 A | 4/2013 |
| KR | 101301337 B1 | 8/2013 |
| KR | 20150058833 A | 5/2015 |
| KR | 20150058834 A | 5/2015 |
| KR | 20150058835 A | 5/2015 |
| KR | 20150121460 A | 10/2015 |
| KR | 20170029718 A | 3/2017 |
| KR | 101761446 B1 | 7/2017 |
| KR | 101761448 B1 | 7/2017 |
| WO | 2015080098 A1 | 6/2015 |

OTHER PUBLICATIONS

Extended European Search Report including Written Opinion for Application No. EP18879814.4, dated Feb. 5, 2020, pp. 1-6.
MacMahon T, Chace M. Poly (ami acid) and polyimide characterization using gas chromatography/mass spectrometry and particle beam liquid chromatography/mass spectrometry. Journal of the American Society for Mass Spectrometry. Apr. 1, 1994;5(4):299-304.
Roberts GD, Lauver RW. Quantitative analysis of PMR-15 polyimide resin by HPLC. Journal of applied polymer science. Jun. 1987;33(8):2893-913.
Korean Search Report for KR20170154651 dated Oct. 17, 2017.
Korean Search Report for KR20170154651 dated May 24, 2018.
International Search Report for PCT/KR2018/011481 dated Jan. 21, 2019.
Jung, Jong-Mo et al., "Characterization of Polyimide: Application of Hydrolysis and Reactive-Pyrolysis for Composition Analysis," Polymer Science and Technology, vol. 16, No. 1, Feb. 2005, pp. 93-100.
Park YJ, Yu DM, Choi JH, Ahn JH, Hong YT. Synthesis and Characterization of 4-Component Polyimide Films with Various Diamine and Dianhydride Compositions. Applied Chemistry for Engineering. 2011;22(6):623-6.
Chinese Search Report for Application No. 201880013109.5, dated Jan. 11, 2021, 1 page.

*Primary Examiner* — Paul S Hyun
(74) *Attorney, Agent, or Firm* — Lerner, David, Littenberg, Krumholz & Mentlik, LLP

(57) ABSTRACT

An analysis method is provided, wherein a measurement sample containing a diamine and an acid dianhydride can be obtained without a separate methyl derivatization process. The analysis method includes pretreating a polyimide film including the polyimide which is a poorly soluble polymer with DMAc after hydrolysis, and determining an amount of monomers contained in the polyimide film.

10 Claims, 1 Drawing Sheet

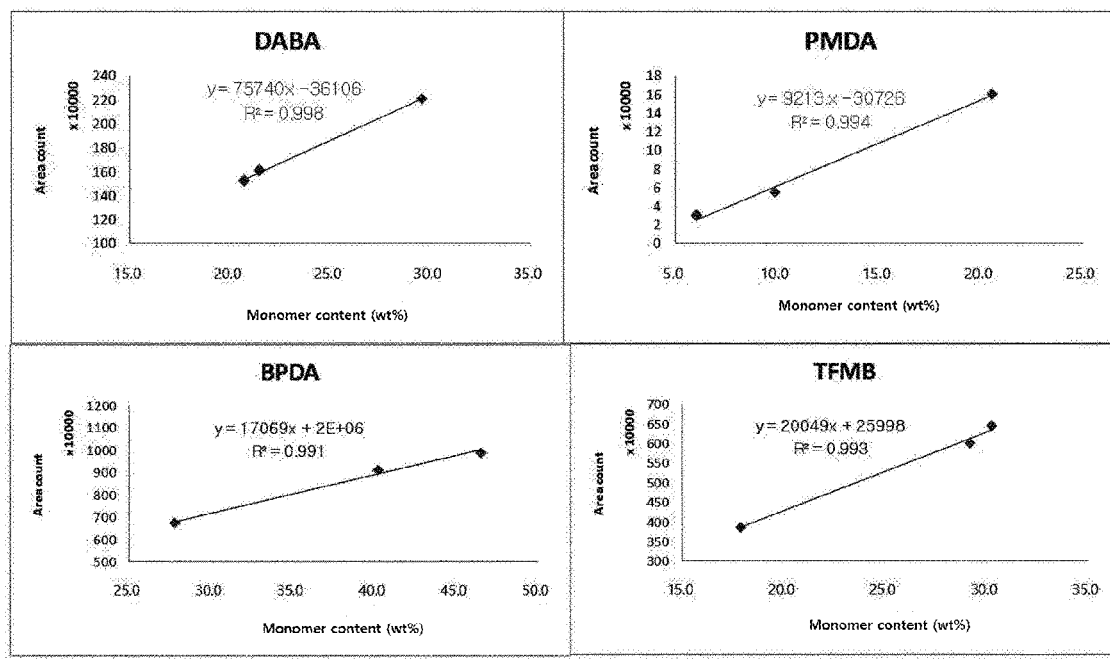

METHOD FOR QUANTITATIVE ANALYSIS OF MONOMERS IN POLYIMIDE FILM

CROSS-REFERENCE TO RELATED APPLICATIONS

This application is a national phase entry under 35 U.S.C. § 371 of International Application Number PCT/KR2018/011481, filed Sep. 28, 2018, which claims priority to Korean Patent Application No. 10-2017-0154651, filed Nov. 20, 2017, the disclosures of which are incorporated herein by reference.

BACKGROUND OF THE INVENTION

1. Field of the Invention

The invention relates to a method for quantitative analysis of monomers in a polyimide film. More particularly, the invention relates to a pretreatment method for quantitative analysis of monomers in a polyimide film using HPLC.

2. Description of the Related Art

Polyimide (PI) film has excellent thermal stability and mechanical properties so that it is widely used in industry. Recently, it is widely used as information electronic material. Such a polyimide film is prepared by polymerization of dianhydride and diamine to obtain polyamic acid (PAA) as a precursor and imidization of PAA under heat treatment to form a film. In the research and development of the polyimide film, a method for analyzing monomer composition of the polyimide film is needed.

In this regard, as the conventional method for analyzing monomer composition of a polyimide film, a method using Pyrolysis GC-MS or a method of analyzing a polyimide film after derivatization with tetramethylammonium hydroxide (TMAH) as disclosed in Korean Patent Application Laying-open No. 1995-0029297 has been employed. However, these methods have troubles in that it is difficult to interpret the obtained data due to the generation of complicated pyrolysis products, and the derivatization of dianhydride does not easily occur, which makes it difficult to identify monomer components.

In addition, a method of analyzing the composition of a polyimide film by using GC/MS after pretreatment of the film through a hydrolysis method for extraction of diamine and a methanolysis method for extraction of dianhydride has been introduced, but this method has a problem that it allows for only qualitative analysis.

SUMMARY OF THE INVENTION

In a first aspect, the invention pertains to a method for quantitative analysis of monomers in a polyimide film by HPLC.

In a further aspect, the invention pertains to a pretreatment method for qualitative and quantitative analysis of a polyimide film using a hydrolysis method.

For the first aspect, the invention provides a method for quantitative analysis of monomers in a polyimide film, comprising the steps of:

a) hydrolyzing a polyimide film prepared by using at least one diamine and acid dianhydride with a strong base;

b) adding DMAc (dimethylacetamide) solvent to the solution containing the hydrolyzed polyimide film and performing ultrasonication of the solution to dissolve it;

c) adding $H_2O$ to the ultrasonicated solution; and d) analyzing the solution prepared in the step c) by using HPLC.

According to one embodiment, the analysis method may be performed by simultaneous derivatization of diamine and acid dianhydride contained in the polyimide film.

According to one embodiment, the strong base may be NaOH.

According to one embodiment, the concentration of the strong base may be from 0.2N to 10N.

According to one embodiment, the hydrolysis of the step (a) may be carried out at 100 to 150° C. for 2 to 24 hours.

According to one embodiment, the ultrasonication of the step (b) may be performed for 30 minutes to 2 hours after the addition of the DMAc to obtain complete dissolution of the hydrolyzed monomers.

According to one embodiment, the method of the invention may further comprise the steps of:

analyzing three or more polyimide films each containing the same monomers as those of said polyimide film and having different monomer composition by using HPLC to obtain a calibration curve; and substituting the area counts of the monomers obtained through HPLC analysis into the calibration curve to determine monomer content.

According to one embodiment, the error for each of the monomer content determined from the calibration curve may be +/−15% or less.

According to one embodiment, the average RSD % of the quantitative analysis results of monomers determined from the calibration curve may be 5% or less.

For the further aspect, the invention provides a pretreatment method for quantitative and qualitative analysis in a polyimide film, comprising the steps of:

a) hydrolyzing a polyimide film prepared by using at least one diamine and acid dianhydride with a strong base;

b) adding DMAc solvent to the solution containing the hydrolyzed polyimide film and performing ultrasonication of the solution to dissolve it; and c) adding $H_2O$ to the ultrasonicated solution.

Effect of the Invention

The invention provides a pretreatment method using DMAc after hydrolysis of a polyimide film comprising diamine and acid dianhydride for HPLC without a separate methyl derivatization step. With such a pretreatment method, it is possible to provide a quantitative analysis method that can be universally utilized for analyzing monomer content in the polyimide film.

BRIEF DESCRIPTION OF THE DRAWINGS

FIGURE is calibration curves of each of the monomers in three standard polyimide films.

DETAILED DESCRIPTION OF THE INVENTION

Since various modifications and variations can be made in the invention, particular embodiments are illustrated in the drawings and will be described in detail by the present disclosure. It should be understood, however, that the invention is not intended to be limited to the particular embodiments, but includes all modifications, equivalents, and alternatives falling within the spirit and scope of the invention. In the present disclosure, detailed description of known functions will be omitted if it is determined that it may obscure the gist of the invention.

The polyimide film, which is a representative poorly soluble polymer, is known to be pretreated by hydrolysis or methanolysis and then analyzed for its composition by GC/MS. However, conventional techniques allow for only qualitative analysis. Therefore, a pretreatment method for quantitative analysis should be accomplished in order to overcome the limit of securing information about monomer content through GC/MS and NMR and to meet the increase in demand for the monomer content information.

In general, the pretreatment method using hydrolysis has been utilized only in qualitative analysis such as analysis of monomer components constituting a poorly soluble polymer. The invention provides an analysis method that can be universally utilized for analyzing monomer contents in a polyimide film, by a pretreatment using hydrolysis to consider a quantitative aspect and obtain information on pyrolysis efficiency.

Specifically, the invention provides a method for quantitative analysis of monomers in a polyimide film, comprising the steps of:

a) hydrolyzing a polyimide film prepared by using at least one diamine and acid dianhydride with a strong base;

b) adding DMAc (dimethylacetamide) solvent to the solution containing the hydrolyzed polyimide film and performing ultrasonication of the solution to dissolve it;

c) adding $H_2O$ to the ultrasonicated solution; and d) analyzing the solution prepared in the step c) by using HPLC.

For quantitative analysis of the polyimide which is a poorly soluble polymer, acid dianhydride salt and diamine can be obtained by derivatization of monomers in polyimide by hydrolysis with a strong base such as NaOH. Among the monomers generated after the hydrolysis, the diamine is easily dissolved in an organic solvent such as methanol or chloroform to facilitate liquid-liquid extraction. However, the acid dianhydride salt is not soluble in an organic solvent, and thus it is difficult to extract it by only hydrolysis. Therefore, a method in which acid dianhydride is subjected to a methyl derivatization step separately and then re-extracted with an organic solvent has been used.

In the invention, by using DMAc solvent as an organic solvent for the liquid-liquid extraction method, it is possible to dissolve all of the diamine and the acid dianhydride salt obtained after hydrolysis of the polyimide film. Accordingly, there is provided a pretreatment method which allows for measurement of acid dianhydride without a separate methyl derivatization step. In addition, unlike the conventional method in which a sample is obtained by the step of extracting diamine monomers and the step of extracting acid dianhydride monomers, the present invention is capable of simultaneously analyzing the monomers in the polyimide film by obtaining a sample containing the diamine and acid dianhydride monomers.

For hydrolysis of the step (a), NaOH as a strong base is used. The hydrolysis efficiency in NaOH may be the most excellent. However, the common strong base may be used, depending on the experimental conditions. For example, LiOH, CsOH, KOH, and the like may be additionally used.

The amount of the strong base to be used in the hydrolysis is not particularly limited as long as sufficient hydrolysis can be accomplished. However, when NaOH is used, the amount may be preferably 10 to 50 times as much as the total amount of the polyimide film.

According to one embodiment, the concentration of the strong base may be from 0.2N to 10N, preferably from 4N to 10N, more preferably from 5N to 7N. For example, the extraction efficiency of monomers may be the highest at a concentration of about 6N, and the extraction efficiency of monomers at this concentration may be improved by 3 to 30 times.

According to one embodiment, the hydrolysis of the step (a) may be carried out at 100° C. to 150° C. for 2 to 24 hours. If the reaction temperature for hydrolysis is lower than 100° C., the hydrolysis time may become longer, and if the temperature is higher than 150° C., decomposition may be excessively promoted, resulting in undesired compounds.

In the step (b), DMAc is added to the solution from the step (a) and ultrasonication is performed for 30 minutes to 2 hours to completely dissolve the hydrolyzed monomers in DMAc. Subsequently, in order to avoid a layer separation problem that can be caused by addition of DMAc as an organic solvent, $H_2O$ is added to suppress the occurrence of layer separation of the sample solution. Finally, quantitative analysis of the polyimide film can be performed by using HPLC of the obtained sample.

The amount of DMAc to be added is not particularly limited as long as the monomers of the hydrolyzed polyimide can be sufficiently dissolved therein. For example, the amount of DMAc to be added may be 10 to 50 times based on the total amount of the polyimide film, or DMAc may be added in a ratio of 1:1 to 1:10 based on the amount of used NaOH, which may be adjusted according to experimental conditions.

The amount of $H_2O$ to be added after the dissolution with DMAc is not particularly limited as long as it can suppress the layer separation, but it is preferable that the amount of $H_2O$ to be added is the same ratio as the amount of DMAc to be added.

The invention provides a method for quantitative analysis of monomers contained in a polyimide film by analyzing with HPLC a sample obtained through the above-described pretreatment method.

For a more precise quantitative analysis, the method of the invention may further comprise the steps of:

analyzing three or more polyimide films each containing the same monomers as those of said polyimide film and having different monomer composition by using HPLC to obtain a calibration curve; and substituting the area counts of the monomers obtained through HPLC analysis into the calibration curve to determine monomer content.

According to the invention, it is possible to obtain calibration curves for the monomers contained in each of the standard polyimide films after pretreatment of three or more standard polyimide films as described above. The monomer content can be more accurately obtained by substituting the area counts of the monomers obtained from the polyimide films used as the sample into the calibration curve.

According to one embodiment, the error for each of the monomer content determined from the calibration curve may be +/−20% or less, preferably +/−15% or less, and the average RSD % of the quantitative results of monomers determined from the calibration curve may be 5% or less.

The invention provides a pretreatment method for quantitative analysis of a polyimide film, which is a poorly soluble polymer, by using a hydrolysis method so that the contents of monomers contained in the polyimide film can be more easily and accurately analyzed.

Hereinafter, embodiments of the invention will be described in detail so that those skilled in the art can easily carry out the invention. The invention may, however, be embodied in many different forms and should not be construed as limited to the embodiments set forth herein.

<Hydrolysis Pretreatment Process>

Approximately 20-30 mg of polyimide film sample (weigh accurately, up to 0.1 mg) was pretreated by hydrolysis in 5 mL of 6N NaOH at 120° C. overnight. After the hydrolysis pretreatment, the sample was cooled to room temperature. 10 mL of DMAc, an organic solvent, was added to the above sample and ultrasonication was performed for 1 hour to confirm that the sample was dissolved. Then, 10 mL of $H_2O$ was added not to separate the layers. HPLC analysis was carried out by using the sample solution prepared as described above.

<HPLC Analysis>

The HPLC system was Waters Alliance 2695, the detector was PDA (Waters 2996) and the software was Waters Empower 3 (Build 3471). The column was Acclaim surfactant (150 mm*4.6). The detection wavelength was 241 nm, the flow rate was 1.0 mL/min, the column temperature was 40° C., and the injection volume was 10 μL. For an eluent, a mobile phase A and a mobile phase B were prepared by mixing acetonitrile (AN, HPLC grade, J. T. Baker) and TFA (Trifluoroacetic acid) in a ratio of 100/0.1, and ultrapure water and TFA in a ratio of 100/0.1, respectively, and filtering by a solvent clarification system. Elution behavior was investigated by gradient elution of the mobile phase A from 5% to 50% in 10 minutes and to 100% in 15 minutes. The area counts of the detected monomers were substituted into the calibration curves to obtain the contents and the weight ratios of the respective monomers.

<Preparation of Calibration Curve>

Three standard products were pretreated with the above-described pretreatment method and quantitatively analyzed under the above HPLC conditions to prepare the calibration curves as shown in FIGURE. The feeding ratios (wt %) of the monomers to each of the three standard polyimide films are shown in Table 1 below.

The calibration curves were checked by using the area counts of each of monomers in std1, std2, and std3 polyimide films as the three standard products. As a result, it was confirmed that the linearity was $R^2$=0.991 or more.

TABLE 1

| wt % | BPDA | PMDA | TFMB | DABA |
|---|---|---|---|---|
| Std 1 | 27.8 | 20.5 | 30.2 | 21.5 |
| Std 2 | 40.2 | 9.9 | 29.2 | 20.7 |
| Std 3 | 46.5 | 6.1 | 17.9 | 29.6 |

* Abbreviations in the Table are as follows.
BPDA: Biphenyl-tetracarboxylic acid dianhydride
PMDA: Pyromellitic dianhydride
TFMB: 2,2'-Bis(trifluoromethyl)benzidine
DABA: 4,4'-Diaminobenzanilide Examples 1 to 3

By using the calibration curves obtained above, the ratios of each of the monomers contained in the polyimide films used in Examples 1 to 3 were determined.

The monomers of the three polyimides used in Examples 1 to 3 and the feeding ratios (wt %) are shown in Table 2 below. The structure of each monomer is shown in Table 3 below.

TABLE 2

| wt % | BPDA | PMDA | TFMB | DABA |
|---|---|---|---|---|
| Example 1 | 27.8 | 20.5 | 30.2 | 21.5 |
| Example 2 | 40.2 | 9.9 | 29.2 | 20.7 |
| Example 3 | 46.5 | 6.1 | 17.9 | 29.6 |

TABLE 3

| # | Component |
|---|---|
| 1 | TFMB |
| 2 | BPDA |
| 3 | PMDA |
| 4 | DABA |

The results of quantitative analysis of the above Examples 1 to 3 using HPLC and the calibration curves are shown in Tables 4 to 6 below.

TABLE 4

| Example 1 | DABA | PMDA | BPDA | TFMB |
|---|---|---|---|---|
| Theoretical value | 21.5 | 20.5 | 27.8 | 30.2 |
| Quantitative value | 20.5 | 18.8 | 25.7 | 29.0 |
| Error (%) | 4.8 | 8.4 | 7.5 | 4.0 |

TABLE 5

| Example 2 | DABA | PMDA | BPDA | TFMB |
|---|---|---|---|---|
| Theoretical value | 20.7 | 9.9 | 40.2 | 29.2 |
| Quantitative value | 19.7 | 10.9 | 45.7 | 26.0 |
| Error (%) | 5.0 | −10.1 | −13.6 | 11.1 |

TABLE 6

| Example 3 | DABA | PMDA | BPDA | TFMB |
|---|---|---|---|---|
| Theoretical value | 29.6 | 6.1 | 46.5 | 17.9 |
| Quantitative value | 26.0 | 6.0 | 47.4 | 15.6 |
| Error (%) | 12.0 | 2.0 | −1.9 | 12.6 |

From the results of quantitative analysis of the three samples of Examples 1 to 3, it was confirmed that the average RSD % ((theoretical value−quantitative value)/theoretical value) was 4.7%.

Comparative Examples 1 to 3

The results of one-point quantitative analysis of each polyimide film used in Examples 1 to 3 are shown in Tables 7 to 9 below.

TABLE 7

| Comparative Example 1 | DABA | PMDA | BPDA | TFMB |
|---|---|---|---|---|
| Quantitative value | 20.7 | 25.8 | 28.5 | 29.6 |
| Theoretical value | 21.5 | 20.5 | 27.8 | 30.2 |
| Error (%) | 3.9 | −26.1 | −2.5 | 2.1 |

TABLE 8

| Comparative Example 2 | DABA | PMDA | BPDA | TFMB |
|---|---|---|---|---|
| Quantitative value | 19.8 | 12.7 | 43.6 | 26.6 |
| Theoretical value | 20.7 | 9.9 | 40.2 | 29.2 |
| Error (%) | 4.2 | −27.8 | −8.4 | 8.9 |

TABLE 9

| Comparative Example 3 | DABA | PMDA | BPDA | TFMB |
|---|---|---|---|---|
| Quantitative value | 26.4 | 4.4 | 44.9 | 16.5 |
| Theoretical value | 29.6 | 6.1 | 46.5 | 17.9 |
| Error (%) | 10.8 | 27.5 | 3.5 | 7.6 |

From the results of the quantitative analysis of the three samples, the average RSD % ((theoretical value−quantitative value)/theoretical value) was confirmed to be 11.1%. It is 6.4% larger than the RSD % in the quantitative analysis using the calibration curve for the three standard products. In particular, the PMDA monomer was quantified with an error of more than 25%, indicating that the one-point quantitative analysis has lower accuracy than the method using a calibration curve.

It will be understood by those skilled in the art that various changes in form and details may be made therein without departing from the spirit or essential characteristics of the invention. Therefore, it should be understood that the above-described embodiments are illustrative in all aspects and not restrictive. In addition, the scope of the present invention is indicated by the following claims rather than the above detailed description.

What is claimed is:

1. A method for quantitative analysis of monomers in a polyimide film, comprising:
   a) hydrolyzing a polyimide film with a strong base to form a solution containing a hydrolyzed polyimide film, wherein the polyimide film comprises at least one diamine and at least one acid dianhydride;
   b) adding DMAc (dimethylacetamide) solvent to the solution containing the hydrolyzed polyimide film and performing ultrasonication to dissolve the at least one diamine and the at least one acid dianhydride to form an ultrasonicated solution;
   c) adding $H_2O$ to the ultrasonicated solution; and
   d) analyzing the solution prepared in the step c) by using HPLC.

2. The method of claim 1, wherein the strong base is NaOH.

3. The method of claim 1, wherein the concentration of the strong base is from 0.2N to 10N.

4. The method of claim 1, wherein the hydrolysis of the step (a) is carried out at 100 to 150° C. for 2 to 24 hours.

5. The method of claim 1, wherein the ultrasonication is performed for 30 minutes to 2 hours after addition of the DMAc to obtain complete dissolution of hydrolyzed monomers.

6. The method of claim 1, wherein the method further comprises:
   analyzing three or more polyimide films each containing same monomers as those of said polyimide film and having different monomer content by using HPLC to obtain a calibration curve; and
   substituting area counts of the monomers obtained through HPLC analysis of the polyimide film of claim 1 into the calibration curve to determine monomer content of said polyimide film.

7. The method of claim 1, wherein the strong base is NaOH, LiOH, CsOH, or KOH.

8. A pretreatment method for quantitative and qualitative analysis of a polyimide film, comprising:
   a) hydrolyzing a polyimide film with a strong base to form a solution containing a hydrolyzed polyimide film, wherein the polyimide film comprises at least one diamine and at least one acid dianhydride;
   b) adding DMAc (dimethylacetamide) solvent to the solution containing the hydrolyzed polyimide film and performing ultrasonication of the solution to dissolve the polyimide film; and
   c) adding $H_2O$ to the ultrasonicated solution.

9. The pretreatment method of claim 8, wherein the strong base is NaOH.

10. The method of claim 8, wherein the strong base is NaOH, LiOH, CsOH, or KOH.

* * * * *